(12) United States Patent
Park et al.

(10) Patent No.: US 8,323,205 B2
(45) Date of Patent: Dec. 4, 2012

(54) SYSTEM AND METHOD FOR IDENTIFYING A POTENTIAL CAUSE OF PULMONARY EDEMA

(75) Inventors: Euljoon Park, Valencia, CA (US); Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 812 days.

(21) Appl. No.: 12/368,916

(22) Filed: Feb. 10, 2009

(65) Prior Publication Data
US 2010/0204593 A1   Aug. 12, 2010

(51) Int. Cl.
*A61B 5/0205*   (2006.01)
(52) U.S. Cl. ........ 600/508; 600/510; 600/512; 600/542; 607/17; 607/18; 607/20
(58) Field of Classification Search ........... 600/508, 600/510, 512, 542; 607/17, 18, 20
See application file for complete search history.

(56) References Cited

U.S. PATENT DOCUMENTS

| 5,466,254 | A | | 11/1995 | Helland |
| 5,957,861 | A | * | 9/1999 | Combs et al. ................. 600/547 |
| 6,748,261 | B1 | | 6/2004 | Kroll et al. |
| 7,272,443 | B2 | | 9/2007 | Min et al. |
| 2004/0220632 | A1 | * | 11/2004 | Burnes ............................. 607/9 |
| 2005/0033368 | A1 | | 2/2005 | Fishler et al. |
| 2005/0124908 | A1 | * | 6/2005 | Belalcazar et al. ........... 600/547 |
| 2005/0216067 | A1 | | 9/2005 | Min et al. |
| 2007/0288059 | A1 | | 12/2007 | Davenport et al. |

FOREIGN PATENT DOCUMENTS

| EP | 1582233 A2 | 10/2005 |
| EP | 1582233 A3 | 6/2006 |
| EP | 1118307 B1 | 10/2007 |

OTHER PUBLICATIONS

Ebner, Erich et al., "Ventricular Evoked Response as Clinical Marker for Hemodynamic Changes in Dilative Cardiomyopathy," PACE. 2004;27:166-174.

* cited by examiner

*Primary Examiner* — Joseph Dietrich

(57) ABSTRACT

A method of identifying a potential cause of pulmonary edema is provided. The method includes obtaining one or more impedance vectors between predetermined combinations of the electrodes positioned proximate the heart. At least one of the impedance vectors is representative of a thoracic fluid level. The method also includes applying a stimulation pulse to the heart and sensing cardiac signals of the heart that are representative of an electrophysiological response to the stimulation pulse. The method further includes monitoring the cardiac signals and at least one of the impedance vectors with respect to time to identify the potential cause of pulmonary edema.

19 Claims, 10 Drawing Sheets

SYSTEM AND METHOD FOR IDENTIFYING A POTENTIAL CAUSE OF PULMONARY EDEMA

CROSS REFERENCE TO RELATED APPLICATIONS

This application is related to U.S. Pat. No. 7,676,260 Ser. No. 11/740,733, filed Apr. 26, 2007, titled "Implantable Cardiac Stimulation Device That Monitors Progression and Regression of Heart Disease Responsive to Differences in Averaged Electrograms and Method".

FIELD OF THE INVENTION

Embodiments of the present invention pertain generally to implantable and external medical devices and more particularly pertain to methods and systems that monitor cardiac signals and measure cardiac impedance.

BACKGROUND OF THE INVENTION

Edema is the abnormal retention of fluid in a patient's body. The fluid may be retained in the patient's thorax, including in the patient's lungs and/or heart. Pulmonary edema is the retention of fluid in the patient's lungs. Pulmonary edema may cause shortness of breath in the patient and result in a need for emergency medical treatment or care.

Pulmonary edema may have a cardiac origin. For example, pulmonary edema may be caused by a cardiac disease. Congestive heart failure typically results in the myocardium of the heart being unable to pump out a sufficient amount of fluid from the heart. For example, the heart may be too weak to fully discharge blood that has accumulated in the heart. As time passes, the build up of fluid in the chambers of the heart causes the heart to be overloaded with the fluid. Excess fluid may drain into the lungs of the patient and cause or exacerbate the patient's pulmonary edema.

Pulmonary edema also may be caused, however, by other conditions unrelated to cardiac disease. For example, pulmonary edema may have a non-cardiac origin. Lung diseases such as emphysema may cause an increase in the build up of fluid in the lungs. This fluid build up may result in pulmonary edema.

The medical therapies that are used to treat pulmonary edema may vary based on the origin or cause of the edema. Pulmonary edema of a cardiac origin may be treated by prescribing medication to the patient such as diuretics, fluid pills, or other medications. These medications may decrease the fluid retained in the heart or lungs. Pulmonary edema of a non-cardiac origin may be treated differently. For example, pulmonary edema that is not from a cardiac-related cause may be treated by inserting a needle or catheter into the pleural space surrounding the lungs and draining the excess fluid.

Known systems and methods do not provide a satisfactory ability to identify the cause of pulmonary edema. For example, known defibrillators and external devices that are communicatively coupled with the defibrillators do not distinguish among the various origins or causes of pulmonary edema. As the proper treatment for pulmonary edema depends on the origin of the edema, a need exists for systems and methods that distinguish between the potential causes or origins of the edema.

SUMMARY

In one embodiment, a method of identifying a potential cause of pulmonary edema is provided. The method includes obtaining one or more impedance vectors between predetermined combinations of the electrodes positioned proximate the heart. At least one of the impedance vectors is representative of a thoracic fluid level. The method also includes applying a stimulation pulse to the heart and sensing cardiac signals of the heart that are representative of an electrophysiological response to the stimulation pulse. The method further includes monitoring the cardiac signals and at least one of the impedance vectors with respect to time to identify the potential cause of pulmonary edema. Optionally, the method includes determining if at least one of the cardiac signals and the impedance vectors follows a predetermined pattern with respect to time. The predetermined pattern may be indicative of a decreasing trend in the values of one or more of the cardiac signals and the impedance vectors respect to time.

In another embodiment, an implantable medical device is provided. The device includes an excitation source, electrodes configured to be positioned proximate a heart, an impedance measuring module and a monitoring module. The excitation source is configured to deliver stimulation pulses to the heart. The electrodes are capable of sensing cardiac signals of the heart that are representative of an electrophysiological response to at least one of the stimulation pulses. The impedance measuring module measures one or more impedance vectors between predetermined combinations of the electrodes. At least one of the impedance vectors is representative of a thoracic fluid level. The monitoring module monitors the cardiac signals and at least one of the impedance vectors with respect to time to identify a potential cause of pulmonary edema. Optionally, the impedance measuring module measures a first impedance vector that traverses at least a portion of a lung and a second impedance vector primarily traversing the heart. Alternatively, the monitoring module may identify the potential cause of pulmonary edema as a cardiac-related condition when the cardiac signals and at least one of the impedance vectors follow one or more predetermined decreasing patterns with respect to time over a preset window.

In another embodiment, a computer readable storage medium for use in a medical device having a plurality of electrodes configured to be positioned proximate a heart, a memory, a programmable microcontroller, and an excitation source is provided. The computer readable storage medium includes instructions to direct the excitation source to apply a stimulation pulse to the heart. The instructions also direct the microcontroller to obtain one or more impedance vectors between predetermined combinations of the electrodes. The impedance vectors are representative of a thoracic fluid level. The instructions further direct the microcontroller to sense cardiac signals of the heart that are representative of an electrophysiological response of the heart to the stimulation pulse. The instructions also direct the microcontroller to monitor the cardiac signals and at least one of the impedance vectors with respect to time to identify a potential cause of pulmonary edema. Optionally, the instructions may direct the microcontroller to identify the potential cause of pulmonary edema as a cardiac-related condition when one or more of the cardiac signals and the impedance vectors indicate that a fluid level in one or more chambers of the heart is increasing with respect to time. In one embodiment, the instructions direct the microcontroller to notify an operator of the medical device to initiate a therapy in response to the potential cause of pulmonary edema.

BRIEF DESCRIPTION OF THE DRAWINGS

The drawings illustrate generally, by way of example, but not by way of limitation, various embodiments discussed in the present document.

DETAILED DESCRIPTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided that are able to identify a potential cause of pulmonary edema or that distinguish between potential cardiac and non-cardiac related causes of pulmonary edema. In one embodiment, the systems and methods described herein provide for the monitoring of thoracic fluid levels and electrophysiologic behavior of a heart to determine whether a potential cause of pulmonary edema is cardiac related. Based on the identification of a potential cause of edema, a therapy or treatment for the patient may be recommended in order to address the potential cause of edema.

Figure 1:
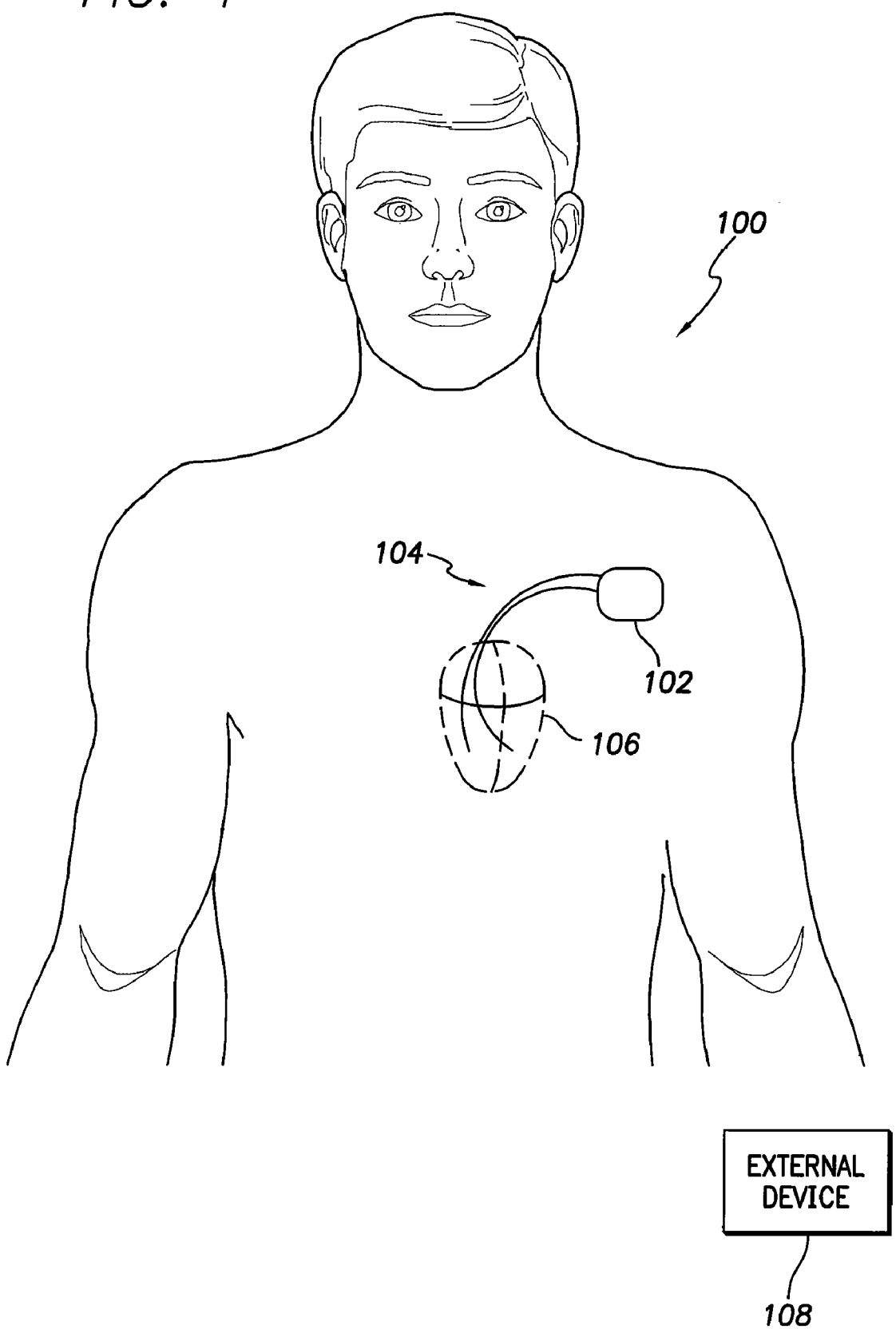
FIG. 1 illustrates an implantable heart monitoring system implemented in accordance with one embodiment and capable of identifying a potential cause of pulmonary edema.

FIG. 1 illustrates an implantable heart monitoring system 100 capable of identifying a potential cause of pulmonary edema. The system 100 includes an implantable medical device (IMD) 102 or other cardiac stimulation device that incorporates internal components for controlling heart failure evaluation functions described below. For example, the IMD 102 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like, implemented in accordance with one embodiment of the present invention. The IMD 102 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. Alternatively, the IMD 102 may be a triple- or quad-chamber stimulation device. Optionally, the IMD 102 may be a multisite stimulation device capable of applying stimulation pulses to multiple sites within each of one or more chambers of the heart 106. The IMD 102 receives signals from leads 104 implanted within a heart 106 of the patient (shown stylistically in phantom lines) from which impedance vectors and cardiac signals are derived. In one exemplary technique described in more detail below, the IMD 102 may measure values of cardiogenic impedance parameters and electrophysiologic response parameters. The cardiogenic impedance parameters may be indicative of a thoracic fluid level of the patient. The electrophysiologic response parameters may represent the electrophysiologic response, or evoked response, of the heart 106 to a non-pacing stimulation pulse. The electrophysiologic response parameters may include one or more characterizations or measurements of cardiac signal waveforms of the heart 106. The cardiogenic impedance parameters and electrophysiologic response parameters may be communicated between the IMD 100 and an external device 108.

The external device 108 may be a monitoring device located at the patient's home or in a hospital environment. The external device 108 analyzes one or more of cardiogenic impedance parameters and electrophysiologic response parameters to determine if a build-up of fluid in one or more of the heart 106 and a lung (shown schematically as lung 238 in FIG. 2) of the patient is potentially caused by the heart 106 or another condition unrelated to the heart 106. For example, the external device 108 may determine that the pulmonary edema suffered by the patient is due to a non-cardiac origin such as emphysema. The external device 108 may then notify an operator of the system 100, such as the patient or a physician, of the potential cause of pulmonary edema. Based thereon, the operator may decide whether to apply or seek therapeutic treatment for the potential cause of pulmonary edema. By way of example only, a physician may drain fluid from the patient's lungs using a needle or catheter if the system 100 identifies the potential cause of pulmonary edema as unrelated to the heart 106, or as being of non-cardiac origin. Alternatively, the physician may treat the patient with medication such as diuretics or fluid pills if the system 100 identifies the potential cause of pulmonary edema to be related to the heart 106, or to have a cardiac origin. In another example, the external device 108 may determine that a patient's potential cause of pulmonary edema is not of cardiac origin. The patient may then avoid an unnecessary and costly trip to the emergency room of a hospital.

Figure 2:
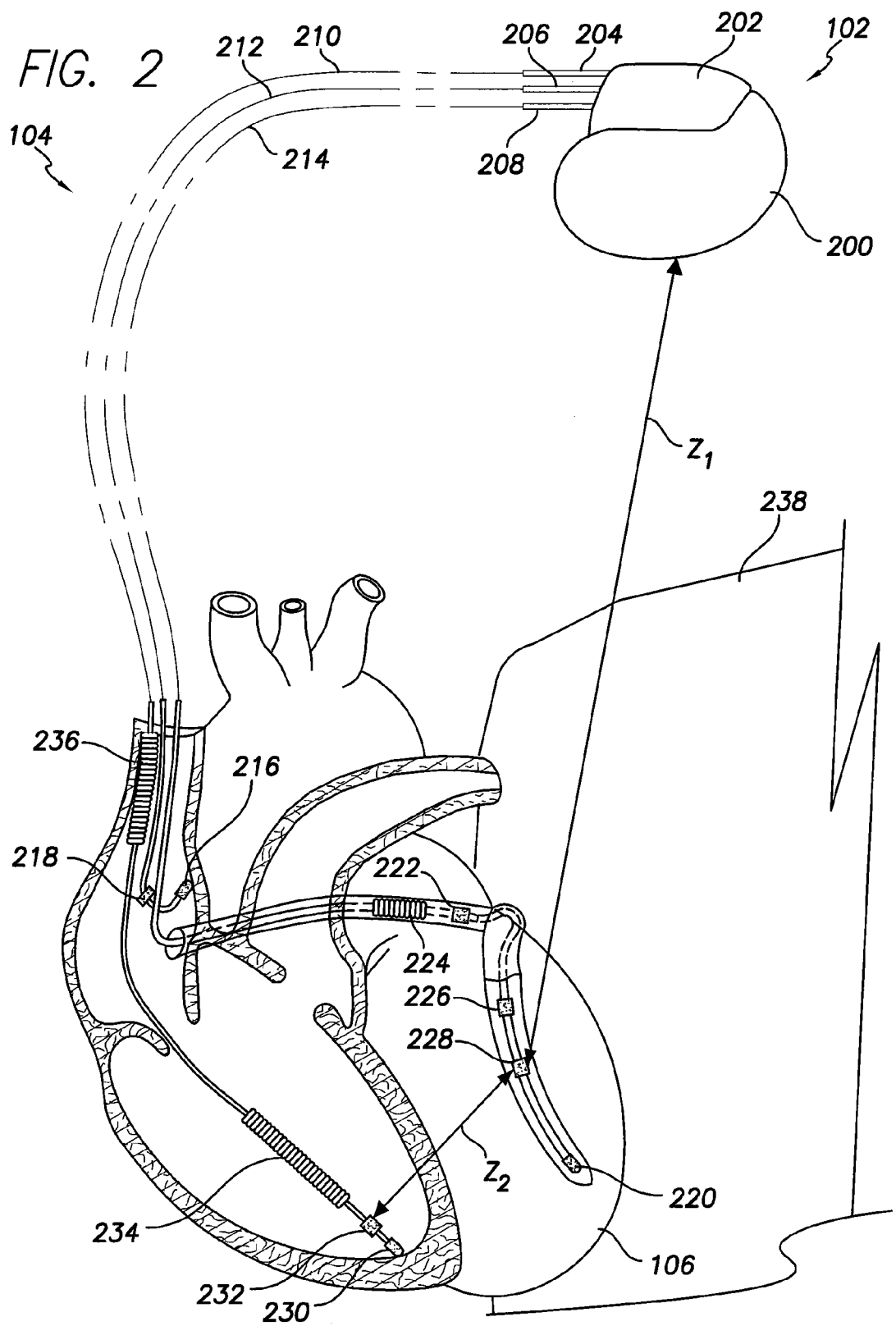
FIG. 2 is an illustration of the implantable medical device shown in FIG. 1 according to one embodiment.

FIG. 2 is an illustration of the IMD 102 that is coupled to the heart 106. The IMD 102 includes a housing 200 that is joined to a header assembly 202 that holds receptacle connectors 204, 206, 208 that are connected to the leads 104. The leads 104 include a right ventricular lead 210 connected to the first receptacle connector 204, a right atrial lead 212 coupled to the second receptacle connector 206, and a coronary sinus lead 214 joined to the third receptacle connector 208. The leads 210, 212, 214 may be located at various locations, such as an atrium, a ventricle, or both to measure physiological parameters of the heart 106. One or more of the leads 210, 212, 214 may detect IEGM signals that form an electrical activity indicator of myocardial function over multiple cardiac cycles.

In order to obtain impedance measurements or vectors, to obtain cardiac signals and to deliver pacing and non-pacing excitation pulses to the heart 106, the IMD 102 includes several electrodes. The housing 200 of the IMD 102 may be one of the electrodes and is often referred to as the "can", "case", or "case electrode." The right atrial lead 212 includes an atrial tip electrode 216 and an atrial ring electrode 218. The coronary sinus lead 214 receives atrial and ventricular cardiac signals and delivers left ventricular pacing therapy using at least a left ventricular (LV) tip electrode 220. Optionally, the coronary sinus lead 214 may deliver left atrial (LA) pacing therapy using at least a left atrial ring electrode 222. In one embodiment, the coronary sinus lead 214 delivers shocking therapy using at least an LA coil electrode 224. The coronary sinus lead 214 may be connected with a plurality of LV ring electrodes 226, 228 disposed between the LV tip electrode 220 and the LA ring electrode 222. The right ventricular (RV) lead 210 is coupled with a RV tip electrode 230, the RV ring electrode 232, and the RV coil electrode 234. The RV lead 210 may include an SVC coil electrode 236. The RV lead 210 is capable of delivering stimulation in the form of pacing and shock therapy to the right ventricle.

The IMD 102 is configured to obtain cardiogenic impedance parameters to identify a potential cause of pulmonary edema as being of cardiac or non-cardiac origin. A cardiogenic impedance parameter includes an impedance vector that represents the impedance measured along a path (generally a linear path) between at least two points and that traverses at least a portion of the heart 106. The two points may be the two locations between which the impedance measurement is obtained. By way of example only, some of the impedance vectors measured by the IMD 102 may include first and second impedance vectors $Z_1$ and $Z_2$ that are measured using predetermined combinations of the housing 200 and the electrodes 216-236. The first and second impedance vectors $Z_1$ and $Z_2$ may be representative of one or more thoracic fluid levels of the patient. For example, the first impedance vector $Z_1$ may be indicative of a level of fluid in the lung 238 and the second impedance vector $Z_2$ may be indicative of a level of fluid in the heart 106.

The first impedance vector $Z_1$ extends along a path that traverses at least a portion of the lung 238. For example, as shown in FIG. 2, the first impedance vector $Z_1$ may pass between the LV ring electrode 228 and the housing 200. Alternatively, the first impedance vector $Z_1$ may extend between a different electrode and the housing 200. For example, the first impedance vector $Z_1$ may extend between a different LV ring electrode 228, the LV tip electrode 220, the RV tip electrode 230, the RV ring electrode 232, the RV coil electrode 234, or some other electrode and the housing 200. The path traversed by the first impedance vector $Z_1$ extends through at least a portion of the lung 238. The second impedance vector $Z_2$ extends along a path that primarily traverses the heart 106 in one embodiment. For example, the second impedance vector $Z_2$ may traverse at least a portion of the left and right ventricles. The second impedance vector $Z_2$ may be measured between the LV ring electrode 228 and the RV ring electrode 232. Alternatively, the second impedance vector $Z_2$ may extend between different electrodes. By way of example only, the second impedance vector $Z_2$ may be measured between the LV tip electrode 220 and the RV tip electrode 230, the LV ring electrode 226 and the RV ring electrode 232, or another combination of electrodes.

The impedance vectors that traverse a portion of the lung 238 include an electrical component associate with the lung 238. Impedance vectors through the lung 238 may provide an indication of the level of fluid or blood in the lung 238. For example, as the level of fluid in the lung 238 increases, the value of the first impedance vector $Z_1$ may decrease. Monitoring the values of the first impedance vector $Z_1$ with respect to time may reveal changes in the first impedance vector $Z_1$, which may be correlated to changes in the fluid level in the lung 238. For example, if the first impedance vector $Z_1$ decreases over a predetermined window of time, then the fluid level in the lung 238 may be increasing during the window. Conversely, if the first impedance vector $Z_1$ does not significantly change or increase during the window, then the fluid level in the lung 238 may decrease or remain substantially constant.

The impedance vectors that primarily traverse the heart 106 include impedance components that are primarily representative of the myocardium and the fluid in the heart 106 along the paths of the impedance vectors. In general, the impedance of fluid in the heart 106 is less than the impedance of the heart tissue. Therefore, impedance vectors that pass through the heart 106 provide an accurate indication of the level of fluid in one or more chambers of the heart 106. For example, as the volume of fluid or blood in the heart 106 increases, the value of the second impedance vector $Z_2$ may decrease. Tracking the values of the second impedance vector $Z_2$ with respect to time may reveal changes in the fluid level in the heart 106. For example, as the level of fluid in the heart 106 builds up, the second impedance vector $Z_2$ may decrease. Conversely, as the level of fluid in the heart 106 remains the same or decreases, the second impedance vector $Z_2$ may remain substantially constant or decrease. Monitoring the second impedance vector $Z_2$ with respect to time also provides an indication of the level of cardiac output, or the amount of fluid that the heart 106 is able to pump out of the heart 106 in a given time period. For example, if the second impedance vector $Z_2$ increases with respect to time, then the heart 106 may be demonstrating sufficient cardiac output in that the heart 106 is able to pump out any excess fluid build up in the heart 106. In another example, if the second impedance vector $Z_2$ remains approximately constant with respect to time, then the heart 106 may be pumping out a sufficient amount of fluid to keep the cardiogenic impedance approximately the same. In a healthy heart 106, the cardiogenic impedance vectors $Z_1$ and $Z_2$ may remain approximately constant with respect to time.

In addition to the cardiogenic impedance parameters, the IMD 102 is configured to sense cardiac signals to identify a potential cause of pulmonary edema as being of cardiac or non-cardiac origin. For example, the IMD 102 may apply one or more stimulation pulses to the heart 106 and measure one or more electrophysiologic response parameters of the heart 106. The stimulation pulse applied by the IMD 102 may be a non-pacing stimulation pulse to one or more chambers of the heart 106. The non-pacing stimulation pulse may be a non-regular stimulation pulse provided outside or in place of a regularly timed or periodic pacing pulse. For example, the non-pacing stimulation pulse may be a non-therapeutic application of a stimulation pulse that is not related to adjusting or maintaining a rhythm of the cardiac cycles of the heart 106. In one embodiment, the non-pacing stimulation pulse is applied to the heart 106 only when an electrophysiologic response parameter is to be measured to identify a potential cause of pulmonary edema. The non-pacing stimulation pulse may be applied to the left ventricle of the heart 106 in one embodiment. For example, the stimulation pulse may be applied to the heart 106 using one or more of the LV tip electrode 220 and the LV ring electrode 228. Alternatively, the stimulation pulse may be applied to a different chamber of the heart 106 and/or using a different electrode.

The electrophysiologic response parameters are measurements of the response of the heart 106 to the stimulation pulse. In one embodiment, the electrophysiologic response parameters indicate a relative amount of myocardial mass in the heart 106. The relative amounts of myocardial mass in the heart 106 or proximate one or more chambers of the heart 106 may represent changes in the amount of fluid held in the chambers. For example, the amount of myocardial mass proximate a chamber of the heart 106 may vary based on the amount of fluid retained in the chamber. As the amount of fluid in the chamber increases, the myocardial walls surrounding the chamber may stretch and become thinner. The stretching and thinning of the myocardial walls reduces the amount of myocardial mass around the chamber. On the other hand, as the amount of fluid in the chamber decreases, the myocardial walls surrounding the chamber may stop stretching and cause an increase in the myocardial mass surrounding the chamber. Therefore, an increase in electrophysiological response parameters obtained during a window of time may represent an increase in the amount of myocardial mass proximate to one or more chambers of the heart 106. Conversely, a decrease in the electrophysiologic response parameters may represent a decrease in the amount of myocardial mass.

In one embodiment, the electrophysiologic response parameters that are measured by the IMD 102 include one or more characteristics of a digitized waveform of the cardiac signals sensed by the IMD 102 after the non-pacing stimulation pulse is applied. After applying the stimulation pulse, the IMD 102 senses cardiac signals of the heart 106 that are evoked in response to the stimulation pulse. The cardiac signals may be referred to as the evoked response (ER) of the heart 106. The cardiac signals may be sensed by one or more of the electrodes 216-236. In one embodiment, the cardiac signals are represented as several digitized waveforms such as a P-wave, a Q-wave, an R-wave, an S-wave and a T-wave.

Figure 3:
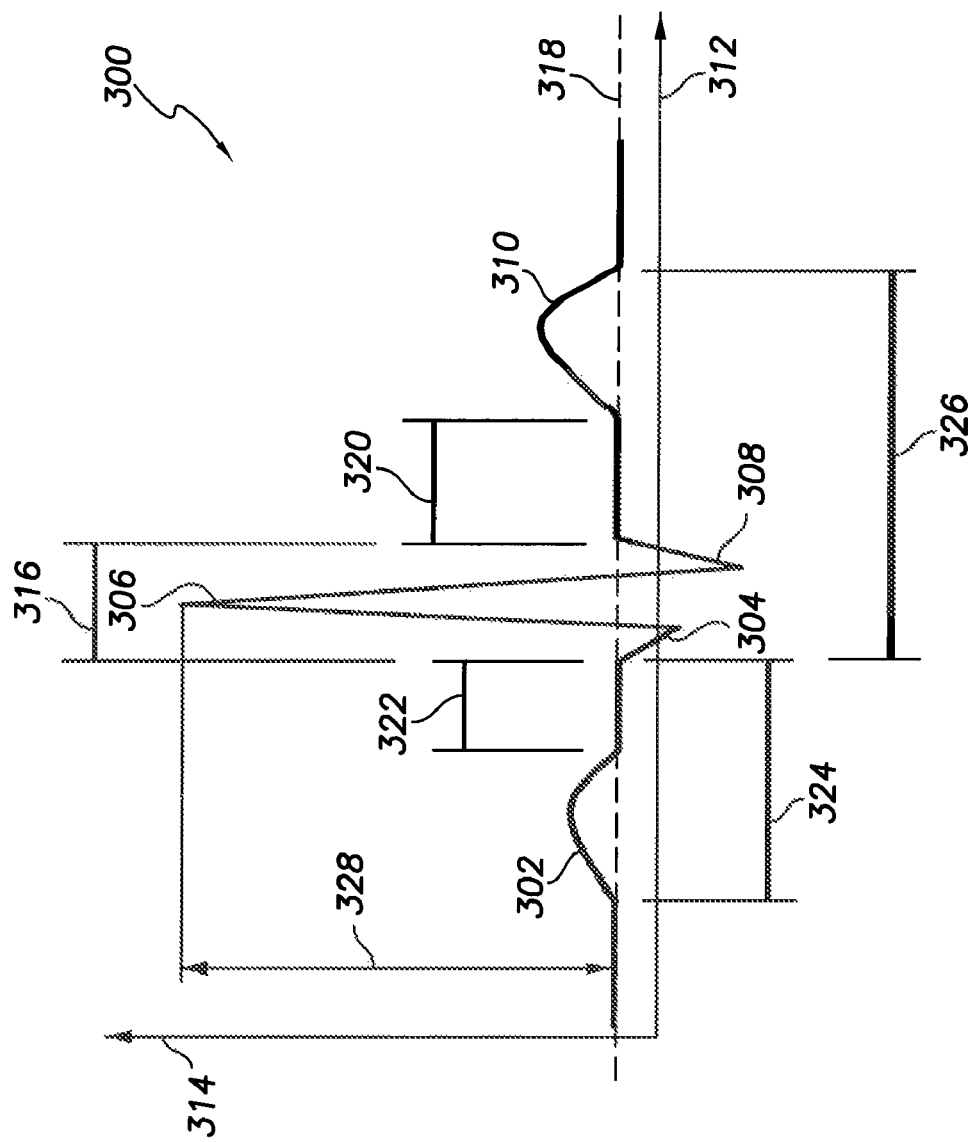
FIG. 3 illustrates a waveform of an example of a single cardiac cycle measured in response to application of a stimulation pulse.

FIG. 3 illustrates a waveform of a single cardiac cycle 300 measured in response to application of a stimulation pulse to the heart 106 (shown in FIG. 1). The cardiac cycle 300 may represent cardiac signals, such as IEGM signals, ECG signals, and the like. The cardiac cycle 300 includes a P-wave 302, a Q-wave 304, an R-wave 306, an S-wave 308, and a T-wave 310. The horizontal axis 312 represents time, while the vertical axis 314 is represents the evoked potential measured in the myocardium of the heart 106. A QRS complex 316 is composed of the Q-wave 304, the R-wave 306, and the S-wave 308. The QRS complex 316 may be used to locate the R-wave 306 to determine a baseline or isoelectric line 318. The portion of the signal between the S-wave 308 and T-wave 310 constitutes an ST segment 320. The portion of the signal between the P-wave 302 and the Q-wave 304 is referred to as a PR segment 322. The signal portion that includes the P-wave 302 and the PR segment 322 is the PR interval 324. The portion that includes the QRS complex 316, the ST segment 320 and the T-wave 310 is referred to as the QT interval 326.

In a heart 106 (shown in FIG. 1) demonstrating sufficient cardiac output to prevent a build up of fluid in the chambers of the heart 106, an amplitude 328 of the R-wave 306 remains approximately the same for a plurality of cardiac cycles evoked by the non-pacing stimulation pulses. For example, the height of the R-wave 306 above the baseline 318 remains approximately the same for each cardiac cycle measured in response to or following application of a non-pacing stimulation pulse to a heart 106 that is able to pump out a sufficient amount of fluid from the heart 106 and prevent a build up of fluid in the heart 106. Conversely, in a heart 106 that is not pumping out enough fluid to prevent a build up of fluid in the heart 106, the amplitude 328 of the R-wave 306 may not remain approximately the same for several cardiac cycles evoked by the non-pacing stimulation pulses. For example, the amplitude 328 may gradually decrease throughout a series of cardiac cycles evoked by the non-pacing stimulation pulses. While one or more of the cardiac cycles may demonstrate an increased amplitude 328 relative to one or more prior and subsequent cardiac cycles, the amplitudes 328 of the R-waves 306 may follow a decreasing pattern or trend throughout a predetermined window of time. The amplitude 328 of the R-wave 306 may decrease due to the inability of the ventricles of the heart 106 to pump out the existing fluid in the heart 106. As the amount of fluid in the heart 106 continues to build up, the myocardium surrounding the ventricles may become stretched and unable to fully contract. As a result, the depolarization of the ventricles is reduced and the amplitude 328 of the R-wave 306 decreases.

In one embodiment, the electrophysiologic response parameters that are measured by the IMD 102 include at least one of a conduction velocity and a conduction time of the myocardium of the heart 106. The conduction velocity represents the speed at which a depolarization wavefront passes through the myocardium of the heart 106. For example, the conduction velocity may be measured by applying an electric potential at a first area or point in the heart 106, which may then initiate depolarization of the myocardium proximate the point of application. The depolarization creates a depolarization wavefront that may pass through the myocardium to another area of the heart 106. The depolarization wavefront may cause a second area of the heart 106 to depolarize. The distance between the point of applying the electric potential, divided by the time required for the resultant depolarization waveform to pass through the myocardium and be detected at the second area, is representative of the conduction velocity. The conduction time represents the time that elapses between applying the electric potential and detecting the myocardial depolarization at the second area. While the discussion here focuses on conduction velocity, conduction time may be used instead.

The conduction velocity may be measured between two points in the same chamber of the heart 106 or between points in two different chambers of the heart 106. In one embodiment, the conduction velocity is measured between inter-ventricle points. For example, the conduction velocity may be measured between one point in the left ventricle and a second point in the right ventricle. The IMD 102 may cause the RV tip electrode 230 to apply the electric potential to the right ventricle. As the right ventricle depolarizes, a depolarization wavefront is created and passes to the left ventricle. The LV tip electrode 220 may sense the depolarization of the left ventricle when the depolarization wavefront is received in the left ventricle. The conduction velocity may be calculated based on the distance between the RV tip electrode 230 and LV tip electrode 220, divided by the time elapsed between application of the electric potential and detection of the depolarization of the myocardium in response thereto.

In general, the conduction velocity and myocardial mass are indirectly related. For example, as the myocardial mass increases, the conduction velocity decreases. Conversely, as the myocardial mass decreases, the conduction velocity increases. The conduction velocity may be used to determine relative changes in the amount of fluid retained in one or more chambers of the heart 106. For example, as more fluid is retained in the ventricles of the heart 106, the myocardium surrounding the ventricles may be stretched and become thinner. The thinning of the myocardial walls surrounding the ventricles may locally reduce the myocardial mass. As a result, the conduction velocity through the myocardium proximate the ventricles may increase. On the other hand, as less fluid is retained in the ventricles, the myocardium becomes less stretched and the myocardial mass may locally increase. As a result, the conduction velocity through the myocardium proximate the ventricles may increase.

Figure 4:
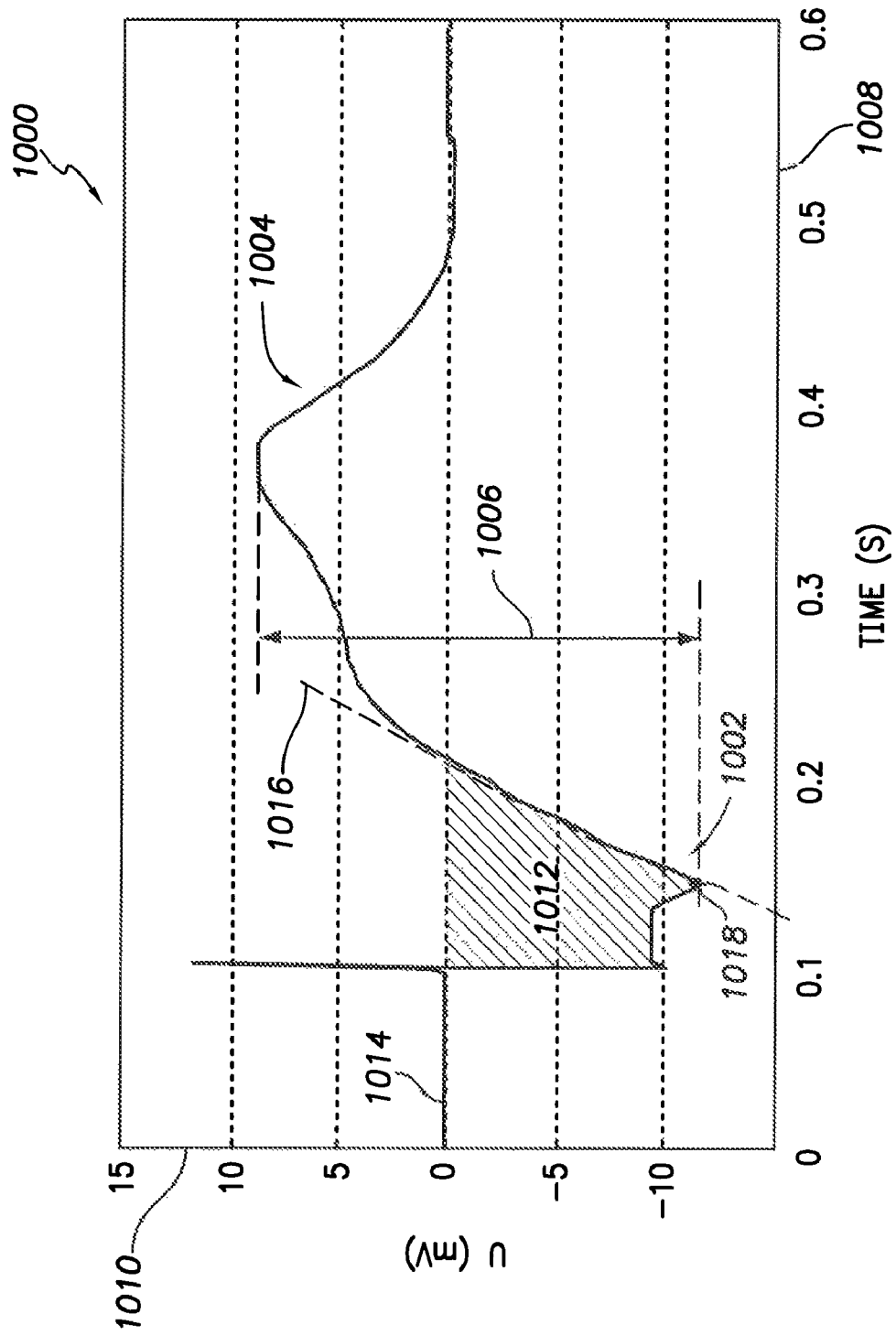
FIG. 4 illustrates an intra-cardiac electrogram (IEGM) representative of cardiac signals of the heart 106 shown in FIG. 1.

FIG. 4 illustrates an intra-cardiac electrogram (IEGM) 1000 representative of cardiac signals of the heart 106 (shown in FIG. 1). The IEGM 1000 is shown on a graph having a horizontal axis 1008 and a vertical axis 1010. The horizontal axis 1008 represents time and the vertical axis 1010 represents the voltage of the cardiac signals measured by the IMD 102. The IEGM 1000 includes an R-wave 1002 and a T-wave 1004. The R- and T-waves 1002, 1004 are measured by the IMD 102 (shown in FIG. 1) after application of a stimulation pulse by the IMD 102. The R- and T-waves 1002, 1004 represent the behavior of the ventricles of the heart 106. Certain electrophysiologic parameters of the IEGM 1000 may be obtained from the IEGM 1000 to identify a potential cause of pulmonary edema as cardiac related or non-cardiac related. The electrophysiologic parameters include measurements of the waveform morphology of the R- and T-waves 1002, 1004.

For example, one electrophysiologic parameter obtained from the IEGM 1000 includes a peak-to-peak parameter 1006. The peak-to-peak parameter 1006 is the sum of the absolute values of the amplitudes of the R-wave 1002 and the T-wave 1004. The amplitude of the R-wave 1002 is the height of the R-wave 1002 below the baseline 1014 and the amplitude of the T-wave 1004 is the height of the T-wave 1004 above the baseline 1014. In the example shown in FIG. 4, the absolute value of the R-wave 1002 amplitude is approximately 12 mV and the T-wave amplitude 1004 is approximately 8 mV. The sum of the R-wave 1002 and T-wave 1004 amplitudes is approximately 20 mV. While the baseline 1014 is shown at approximately 0 mV in FIG. 4, the baseline 1014 may be slightly above or below 0 mV. In a patient suffering from pulmonary edema having a cardiac origin, the peak-to-peak parameter 1006 may vary among several evoked responses. For example, the peak-to-peak parameter 1006 may increase or decrease over time in response to several stimulation pulses applied to the heart 106.

Another example of an electrophysiologic parameter obtained from the IEGM 1000 includes a paced depolarization integral (PDI) 1012. The PDI 1012 represents the area between the R-wave 1002 and a baseline 1014 of the IEGM 1000. For example, prior to applying a stimulation pulse, the IEGM 1000 may have a relatively steady value at the baseline 1014 during the time period of zero to approximately 0.1 seconds. After applying the stimulation pulse at approximately 0.1 seconds, the IEGM 1000 rapidly increases then decreases into the R-wave 1002. The IEGM 1000 returns to the baseline 1014 before beginning the T-wave 1004 at approximately 0.2 seconds. The PDI 1012 is determined by calculating the area between the R-wave 1002 and the baseline 1014. For example, the PDI 1012 may be calculated by integrating under the R-wave 1002. In a patient suffering from pulmonary edema having a cardiac origin, the PDI 1012 may vary among several evoked responses. For example, the size and/or shape of the R-wave 1002 may change over time in response to several stimulation pulses applied to the heart 106. As the R-wave 1002 changes, the PDI 1012 also may change and be indicative of the origin of pulmonary edema.

Another example of an electrophysiologic parameter obtained from the IEGM 1000 includes a waveform slope 1016. The waveform slope 1016 represents the change in amplitude over a change in time for a portion of the R-wave 1002 or T-wave 1004. In the illustrated embodiment, the waveform slope 1016 is a straight line fit to a portion of the R-wave 1002 that occurs after the R-wave peak 1018. Alternatively, the waveform slope 1016 may be calculated for a different portion of the R-wave 1002 or for a different waveform such as the T-wave 1004. In a patient suffering from pulmonary edema having a cardiac origin, the waveform slope 1016 can vary among several evoked responses. For example, the waveform slope 1016 shown in FIG. 4 may be representative of a depolarization delay in the ventricles of the heart 106. The morphology of the R-wave 1002 may change over time in response to several stimulation pulses applied to the heart 106. As the R-wave 1002 morphology changes, the waveform slope 1016 also may change and be indicative of the origin of pulmonary edema.

Figure 5:
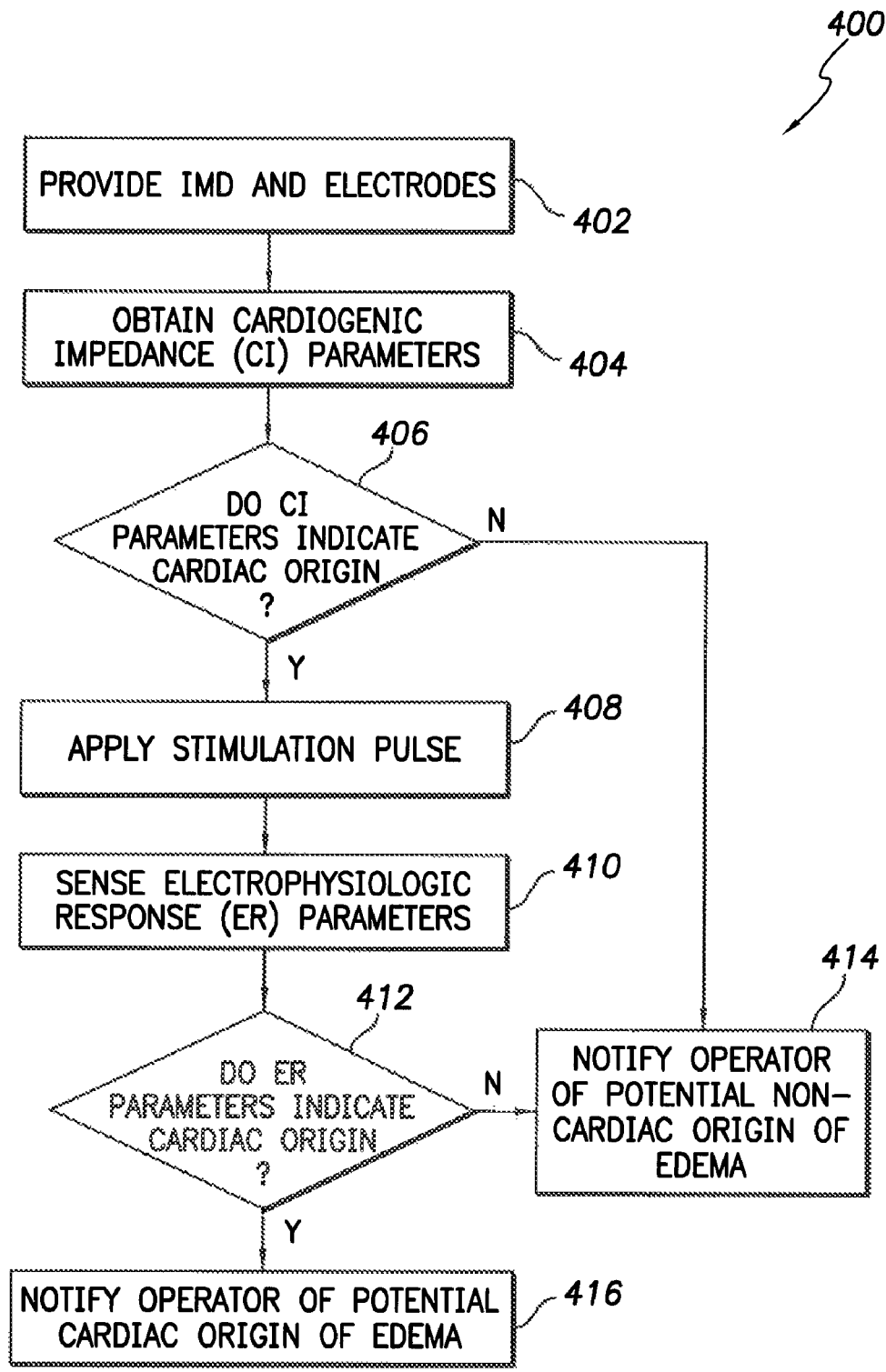
FIG. 5 illustrate a process for identifying a potential cause of pulmonary edema in accordance with one embodiment.

FIG. 5 illustrate a process 400 for identifying a potential cause of pulmonary edema in accordance with an embodiment. At 402, the IMD 102 (shown in FIG. 1) and electrodes are provided. The electrodes may include the housing 200 (shown in FIG. 2) of the IMD 102 and one or more of the electrodes 216-236 (shown in FIG. 2). At 404, one or more cardiogenic impedance parameters are obtained. In one embodiment, the cardiogenic impedance parameters include the first and second impedance vectors $Z_1$ and $Z_2$ (shown in FIG. 2). The cardiogenic impedance parameters may be obtained for each cardiac cycle in a set of cardiac cycles. The set of cardiac cycles may be defined by a number of consecutive cardiac cycles or by a predetermined window of time. Alternatively, the cardiogenic impedance parameters may be representative of the values of various parameters measured during a set of cardiac cycles. For example, the cardiogenic impedance parameters may be an average, mean, median, maximum, minimum, deviation, and the like, of one or more impedance vectors measured for multiple cardiac cycles in a set of cardiac cycles. The cardiogenic impedance parameters may be obtained in real time. For example, at 404, the cardiogenic impedance parameters may be measured during examination of the patient. Alternatively, the cardiogenic impedance parameters may be previously measured and stored in a memory. At 404, the cardiogenic impedance parameters may then be obtained from the memory.

At 406, one or more of the cardiogenic impedance parameters are examined to determine if the parameters indicate that a potential cause of pulmonary edema is of cardiac origin. In one embodiment, the examination performed at 406 includes determining if one or more of the impedance vectors obtained at 404 follows a predetermined pattern with respect to time. For example, the values of one or more of the first and second impedance vectors $Z_1$, $Z_2$ may be examined to determine if one or both of the impedance vectors follows a predetermined decreasing pattern. The predetermined pattern may represent a general trend in the values of the impedance vectors. For example, the pattern may represent a general decreasing trend in the values of the impedance vectors. As described above, a decreasing trend in the impedance vectors $Z_1$ and $Z_2$ may be associated with an increase in the amount of fluid in one or more chambers of the heart 106.

Figure 6:
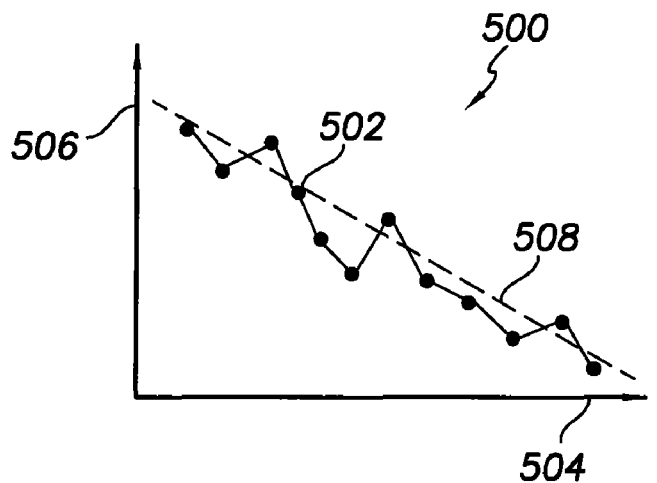
FIG. 6 illustrates three examples of cardiogenic impedance parameters that are measured with respect to time.
Figure 6:
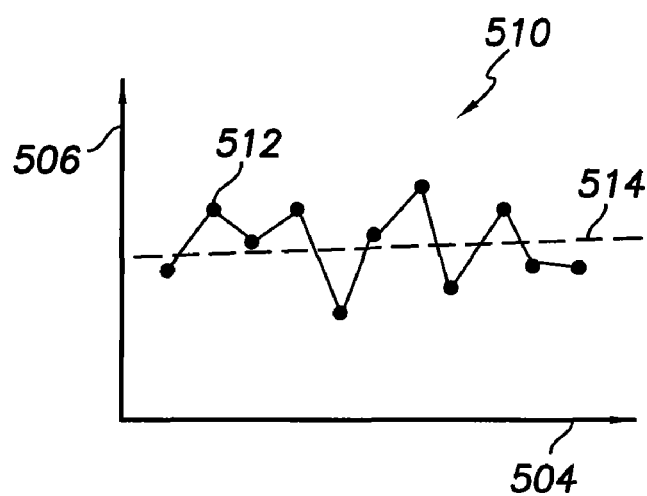
Figure 6:
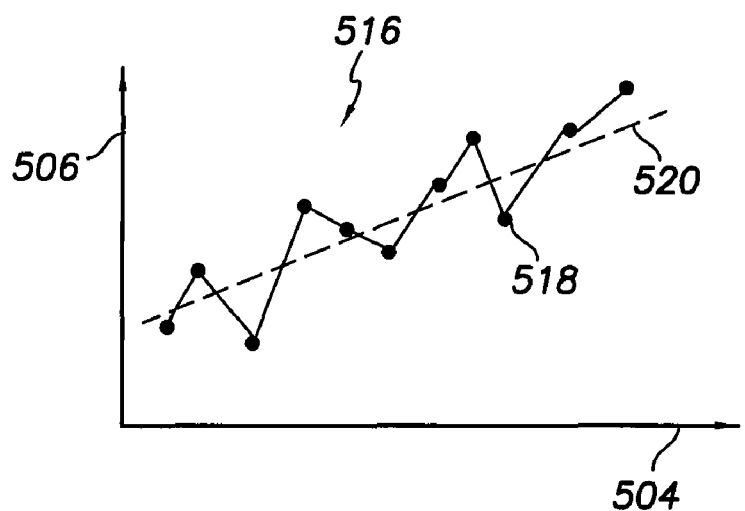

FIG. 6 illustrates three examples of cardiogenic impedance parameters that are measured with respect to time. A first graphical representation 500 illustrates several values 502 of an impedance vector measured with respect to time. For example, the values 502 may represent the values of the first or second impedance vector $Z_1$ or $Z_2$ measured during a window of time. The horizontal axis 504 represents time while the vertical axis 506 represents the range of values of the impedance vector. A trend or pattern 508 of the values 502 is determined in order to compare the values 502 with the predetermined pattern described above. The trend 508 may be calculated using a variety of techniques, including but not limited to a least squares model, a weighted least squares model, an R-squared model, an autoregressive moving average model, or a generalized linear or nonlinear model. As shown in FIG. 6, the trend 508 demonstrates a generally decreasing pattern in the represented impedance parameter with respect to time. In one embodiment, the predetermined pattern that is compared to the values 502 at 406 is a predetermined decreasing pattern. For example, at 406, the trend 508 is fit to the values 502 and it is determined if the trend 508 shows a decreasing pattern in the values 502. Therefore, while the values 502 of the impedance parameters may occasionally increase during the window of time examined at 406, the general trend 508 in the values 502 is to follow a predetermined decreasing pattern.

A second graphical representation 510 illustrates a different set of values 512 of the impedance vector measured with respect to time. In contrast to the first representation 500, the values 512 in the second representation 510 have a trend 514 that does not follow a predetermined decreasing pattern with respect to time. As shown in FIG. 6, the trend 514 in the values 512 does not decrease with respect to time and may be approximately constant with respect to time. A third graphical representation 516 illustrates a different set of values 518 of the impedance vector measured with respect to time. In contrast to the first and second representations 500, 510, the values 518 in the third representation 516 have a trend 520 that does not follow a predetermined decreasing pattern with respect to time. As shown in FIG. 6, the trends 514, 520 in the values 512, 518 of the second and third representations 510, 516 do not decrease with respect to time. For example, the second trend 514 may be approximately constant with respect to time while the third trend 520 may be increasing with respect to time.

Returning to FIG. 5, if, at 406, the cardiogenic impedance parameters do not follow a predetermined decreasing pattern over a window of time, then the potential cause of pulmonary edema is identified as being a non-cardiac related condition. For example, if the parameters follow a pattern other than the predetermined decreasing pattern, the potential cause may be identified as a non-cardiac related cause. The determination of whether the cardiogenic impedance parameters follow a predetermined decreasing pattern may be made by calculating the slope of the trend in the cardiogenic impedance parameters. For example, the slope of the trend 508, 514 or 520 (shown in FIG. 6) may be calculated. This slope is then compared to a predetermined slope. The predetermined slope may have a negative value, or be a decreasing slope. If the slope calculated for the trend 508, 514, 520 exceeds the predetermined slope, then the determination at 406 is that the cardiogenic impedance parameters do not follow the predetermined decreasing pattern.

In one embodiment, if either of the first and second impedance vectors $Z_1$, $Z_2$ does not follow one or more predetermined decreasing patterns with respect to time, then the potential cause is identified as not being of a cardiac origin. Alternatively, if both of the first and second impedance vectors $Z_1$, $Z_2$ do not follow predetermined decreasing patterns, then the potential cause is identified as not being of a cardiac origin. In another embodiment, if at least the first impedance vector $Z_1$ does not follow a predetermined decreasing pattern, then the potential cause of pulmonary edema is identified as being a non-cardiac related cause.

On the other hand, if, at 406, the cardiogenic impedance parameters do follow a predetermined decreasing pattern, then a stimulation pulse is applied to the heart 106 (shown in FIG. 1) at 408. For example, if the slope of the trend 508, 514, 520 (shown in FIG. 6) fit to one or more of the cardiogenic impedance parameters does not exceed the predetermined slope, then, at 406, it is determined that the parameters do follow the predetermined decreasing pattern. In one embodiment, if both of the first and second impedance vectors $Z_1$, $Z_2$ follow one or more predetermined decreasing patterns with respect to time, then a non-pacing stimulation pulse is applied at 408. In another example, if at least the first impedance vector $Z_1$ follows a predetermined decreasing pattern, then the non-pacing stimulation pulse may be applied at 408.

At 410, in connection with the stimulation pulse applied at 408, one or more electrophysiologic response parameters are sensed by the IMD 102 (shown in FIG. 1). As described above, the electrophysiologic response parameters may include measurements that are representative of myocardial mass proximate one or more chambers in the heart 106 (shown in FIG. 1). For example, the parameters sensed at 410 may include one or more of the amplitude 328 (shown in FIG. 3) of an R-wave 306 (shown in FIG. 3), the conduction velocity of the myocardium proximate one or more chambers of the heart 106, and the conduction time of the myocardium. The parameters may be obtained during a cardiac cycle subsequent to and in response to the non-pacing stimulation pulse applied at 408.

At 412, one or more of the electrophysiologic response parameters are examined to determine if the parameters confirm that the potential cause of pulmonary edema is a cardiac-related condition. The electrophysiologic response parameters examined at 412 may include two or more different parameters. For example, measurements of two or more of the conduction velocity, the peak-to-peak parameter 1006 (shown in FIG. 4), the PDI 1012 (shown in FIG. 4) and the waveform slope 1016 (shown in FIG. 4) may be examined at 412. The electrophysiologic response parameters may be monitored to confirm a prior identification of the potential cause of pulmonary edema as being of cardiac origin. For example, if the examination of the cardiogenic impedance parameters at 406 results in a determination that the potential cause of pulmonary edema may be of cardiac origin, the electrophyisiologic response parameters may be examined to confirm or refute this determination.

In one embodiment, the examination performed at 412 is similar to the examination performed at 406 in connection with the cardiogenic impedance parameters. For example, the examination at 412 may include determining if one or more of the electrophysiologic response parameters follows a predetermined decreasing pattern with respect to time. In another example, the examination at 412 may include comparing the slope of the trend 508, 514, 520 (shown in FIG. 6) fit to each electrophysiologic response parameter to a predetermined slope. If the calculated slope is greater than the predetermined slope, then, at 412, the electrophysiologic response parameter is not found to follow the predetermined decreasing pattern. Conversely, if the calculated slope does not exceed the predetermined slope, then the electrophysiologic response parameter is found to follow the predetermined decreasing pattern. The predetermined decreasing pattern and/or slope may be the same or different than the patterns and slopes used to examine the cardiogenic impedance parameters.

Moreover, two or more of the electrophysiologic response parameters may be compared to the same or different predetermined patterns at 412. In one embodiment, the values of one or more of the R-wave amplitude 328 (shown in FIG. 3), the conduction velocity and the conduction time may be examined to determine if one more follows a predetermined decreasing pattern. For example, the values may be monitored to determine if the values represent a general decreasing trend with respect to time over a predetermined window of time. As described above, decreasing values of the R-wave amplitude 328, the conduction velocity or the conduction time may represent a decrease in the amount of myocardial mass proximate to one or more chambers of the heart 106 (shown in FIG. 1). The reduction of myocardial mass near chambers of the heart 106 may be related to a build up of fluid in the chambers.

In one embodiment, if the R-wave amplitude 328 (shown in FIG. 3) and at least one of the conduction velocity and the conduction time demonstrate a decreasing trend with respect to time, then the identification of the potential cause of pulmonary edema as being of cardiac origin is confirmed. Conversely, if only one of the R-wave amplitude 328 and the conduction velocity demonstrates a decreasing trend with respect to time, then the identification of the potential cause of pulmonary edema as cardiac-related is not confirmed. For example, if the electrophysiologic response parameters follow a pattern other than the predetermined decreasing pattern, the potential cause may be identified as a non-cardiac related cause.

In another embodiment, if at least one of the R-wave amplitude 328, the conduction velocity and the conduction time exhibits a decreasing trend with respect to time, then the identification of the potential cause as being a cardiac-related cause is confirmed. If none of the R-wave amplitude 328, conduction velocity and conduction time show a decreasing trend, then the identification of the potential cause as being a cardiac-related cause is not confirmed, and the potential cause may be identified as non-cardiac related.

If the potential cause of pulmonary edema is not identified as being a cardiac-related cause at 406, or if the identification of the potential cause of pulmonary edema as being of a cardiac origin is not confirmed at 412, then, at 414, an operator is notified that the potential cause of the pulmonary edema is of a non-cardiac origin. For example, the external device 108 (shown in FIG. 1) may provide an audible and/or visual notification to a physician that the potential cause of the patient's pulmonary edema is not related to the patient's heart 106 (shown in FIG. 1). In one embodiment, the external device 108 provides a recommended course of treatment to the operator in response to the identified potential cause of pulmonary edema. For example, the external device 108 may display instructions for treating non-cardiac originated pulmonary edema on an output device such as a monitor. The instructions may direct the operator to drain the fluid in the patient's lungs or thoracic cavities by inserting a needle or other method, for example. In one embodiment, the external device 108 may direct the operator to perform one or more other examinations on the patient to determine the potential cause of the patient's pulmonary edema.

On the other hand, if the identification of the potential cause of pulmonary edema as being of a cardiac origin is confirmed at 412, then, at 416, an operator is notified that the potential cause of the pulmonary edema is of a cardiac origin. For example, the external device 108 (shown in FIG. 1) may provide an audible and/or visual notification to a physician that the potential cause of the patient's pulmonary edema is related to the patient's heart 106 (shown in FIG. 1). In one embodiment, the external device 108 provides a recommended course of treatment to the operator in response to the identified potential cause of pulmonary edema. For example, the external device 108 may display instructions for treating heart congestion on an output device such as a monitor. The instructions may direct the operator to provide medication to the patient such as a diuretic and/or direct the patient to reduce or limit the intake of fluid, for example. In one embodiment, the external device 108 may cause a warning or notification to be communicated to the patient or physician via a network. The external device 108 may communicate the identification of the potential cause of the patient's pulmonary edema to the patient's physician or to the patient. The identification may be communicated to a hand-held device such as a cellular or mobile phone, for example.

In an alternative embodiment, the process 400 may include applying a non-pacing stimulation pulse to the heart 106 (shown in FIG. 1) at 408, sensing the electrophysiologic response parameters of the heart 106 in response to the pulse at 410 and examining the electrophysiologic response parameters at 412 even if the cardiogenic impedance parameters do not follow a predetermined decreasing pattern at 406. For example, even if the process 400 determines at 406 that the potential cause of the patient's pulmonary edema is not of a cardiac origin at 406, the process 400 may continue to examine the electrophysiologic response parameters of the heart 106 in accordance with the operations at 408, 410 and 412. In such an embodiment, the electrophysiologic response parameters are examined at 412 in order to determine if the patient is suffering from low cardiac output but not from pulmonary edema. For example, the patient may have fluid building up in the patient's heart 106 while fluid is not building up in the patient's lung 238 (shown in FIG. 2). Low cardiac output may be representative of a heart 106 that is not pumping out a sufficient amount of fluid from the heart 106 in order to avoid a build up of fluid in the heart 106. A patient exhibiting low cardiac output may require medical treatment or therapy that differs from that of the therapies used to treat pulmonary edema.

If, for example, the first impedance vector $Z_1$ (shown in FIG. 1) does not follow a predetermined decreasing pattern with respect to time, but the second impedance vector $Z_2$ (shown in FIG. 1) does follow a predetermined decreasing pattern, then the process 400 may determine at 406 that fluid may be building up in the heart 106 (shown in FIG. 1) but not in the lungs 238 (shown in FIG. 2). As a check on this determination, the process 400 may continue on to the operations at 408-412 to determine if the electrophysiologic response parameters demonstrate an increasing amount of fluid in the heart 106. If, at 412, it is determined that fluid is building up in the heart 106, then at 416, the process 400 may notify the operator that the patient is suffering from low cardiac output without evidence of pulmonary edema. The process 400 also may provide suggested treatments for the patient in response to this determination.

Figure 7:
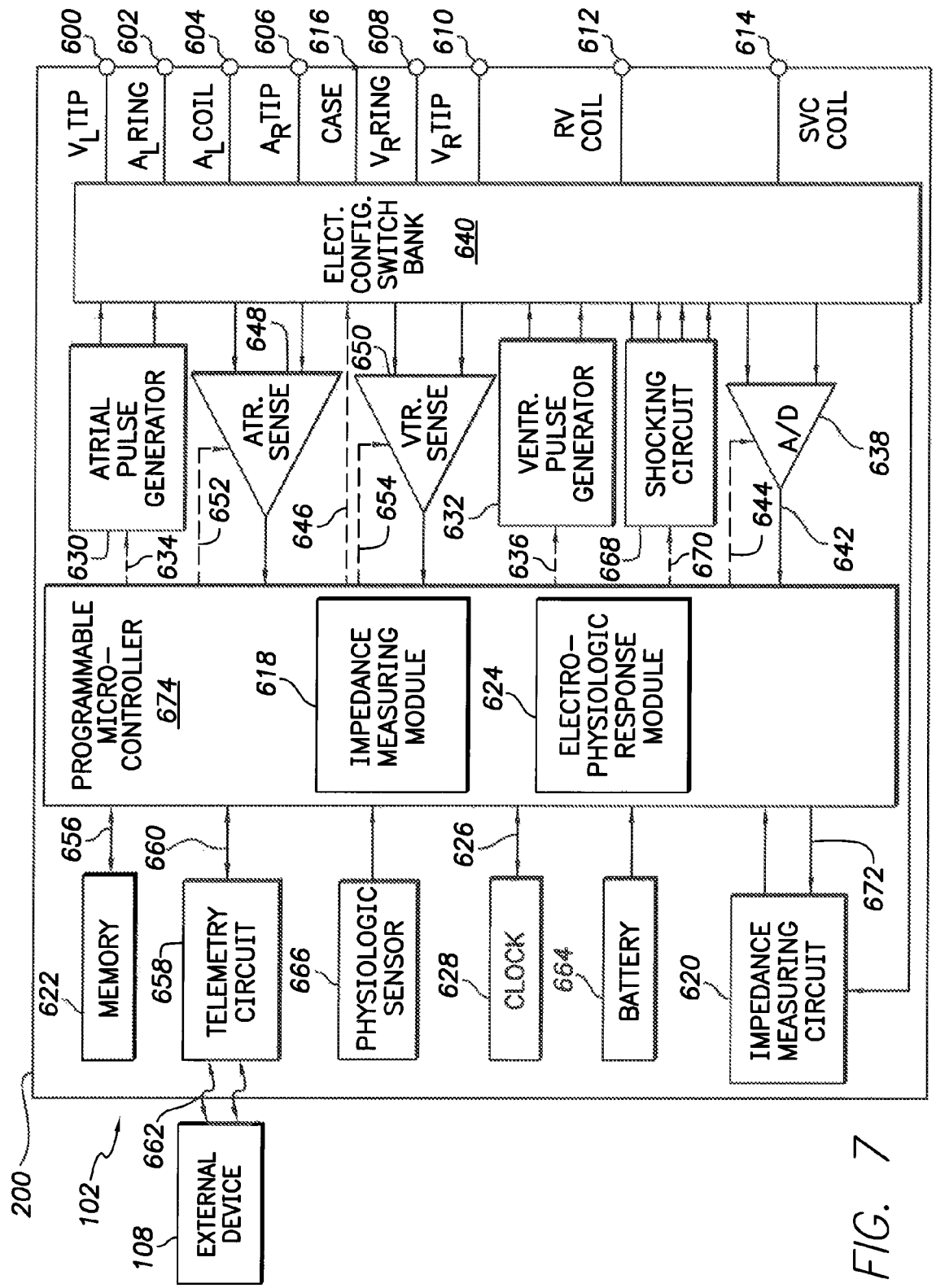
FIG. 7 illustrates a block diagram of exemplary internal components of the implantable medical device shown in FIG. 1.

FIG. 7 illustrates a block diagram of exemplary internal components of the IMD 102. The IMD 102 includes the housing 200, which in turn may further include a connector (not shown) having a plurality of inputs. The inputs may include one or more of a left ventricle tip input terminal ($V_L$ TIP) 600, a left atrial ring input terminal ($A_L$ RING) 602, a left atrial coil input terminal ($A_L$ COIL) 604, a right atrial tip input terminal ($A_R$ TIP) 606, a right ventricular ring input terminal ($V_R$ RING) 608, a right ventricular tip input terminal ($V_R$ TIP) 610, an RV coil input terminal 612 and an SVC coil input terminal 614. A case input terminal 616 may be coupled with the housing 200 of the IMD 102. The input terminals 600-616 may be electrically coupled with the electrodes 216-236 (shown in FIG. 2). For example, the LV tip input terminal 600 may be connected with the electrodes 220, 226, 228; the LA ring input terminal 602 may connected with the electrode 222; the LA coil input terminal 604 may be connected with the electrode 224; the RA tip input terminal 606 may be connected with the electrodes 216, 218; the RV ring input terminal 608 may be connected with the electrode 232; the RV tip input terminal 610 may be connected with the electrode 230; the RV coil input terminal 612 may be connected with the electrode 234; and the SVC coil input terminal 614 may be connected with the electrode 236.

The IMD 102 includes a programmable microcontroller 674, which controls the operation of the IMD 102 based on acquired cardiac signals. The microcontroller 674 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. Among other things, the microcontroller 674 receives, processes, and manages storage of digitized data from the various electrodes 216-236 (shown in FIG. 2). The microcontroller 674 may include one or more modules and processors configured to perform one or more of the actions and determinations described above in connection with the process 400. An impedance measuring module 618 controls measurement of one or more of the cardiogenic impedance parameters. For example, the impedance measuring module 618 may direct an impedance measuring circuit or circuitry 620 to measure impedance vectors between predetermined combinations of the housing, or case electrode, 200 and the electrodes 216-236. The impedance measuring circuit 620 is enabled by the microcontroller 674 via a control signal 672. The impedance measuring module 618 may select the combinations of electrodes 200, 216-236 to be used in measuring the impedance vectors. In one embodiment, the impedance measuring module 618 also calculates the values of the first and second impedance vectors $Z_1, Z_2$ based on the potential measured by one or more of the electrodes 200, 216-236. The impedance measuring module 618 communicates the cardiogenic impedance parameters to at least one of a memory 622 and the external device 108.

An electrophysiologic response module 624 controls measurement of one or more of the electrophysiologic response parameters. For example, the electrophysiologic response module 624 may control which cardiac signals received by the input terminals 600-614 are used to sense the R-wave amplitude 328 (shown in FIG. 3), the conduction velocity or conduction time of the heart 106 (shown in FIG. 1). The electrophysiologic response module 624 may calculate the conduction velocity or measure the conduction time based on a timing signal 626 received from a clock 628. The clock 628 may measure time relative to the cardiac cycles of the heart 106, the cardiogenic impedance parameters or the electrophysiologic response parameters measured by the IMD 102. The clock 628 measures elapsed amounts of time based on start and stop control signals from the microcontroller 674 to monitor the cardiogenic impedance parameters and the electrophysiologic response parameters of the heart 106. The electrophysiologic response module 624 may calculate waveform parameters such as the peak-to-peak parameter 1006 (shown in FIG. 4), the PDI 1012 (shown in FIG. 4) and the waveform slope 1016 (shown in FIG. 4).

The electrophysiologic response module 624 directs an excitation source to deliver the stimulation pulse or pulses to the heart 106 in order to obtain the electrophysiologic response parameters. For example, the electrophysiologic response module 624 may control one or more of an atrial pulse generator 630 and a ventricular pulse generator 632 to generate the non-pacing stimulation pulses described above. The pulse generators 630, 632 are controlled via appropriate control signals 634, 636 to trigger or inhibit the stimulation pulses. The pulse generators 630, 632 also may provide stimulation pulses to providing a pacing therapy to the patient.

The electrophysiologic response module 624 may receive signals from predetermined combinations of the case electrode 200 and the electrodes 216-236 (shown in FIG. 2) via an analog-to-digital (A/D) data acquisition system 638. The cardiac signals obtained by the electrodes 200, 216-236 are applied to the inputs of the data acquisition system 638. For example, the cardiac signals such as the R-wave amplitude 328 (shown in FIG. 3), the electrophysiologic parameters representative of cardiac cycle waveforms, the conduction velocity or the conduction time may be sensed by the electrodes 200, 216-236 and communicated to the data acquisition system 638 after and in connection with the application of a non-pacing stimulation pulse. The cardiac signals are communicated through the input terminals 600-616 to an electronically configured switch bank, or switch, 640 before being received by the data acquisition system 638. The data acquisition system 638 converts the raw analog data of the signals obtained by the electrodes 200, 216-236 into digital signals and communicates the signals as evoked response signals 642 to the electrophysiologic response module 624. A control signal 644 from the microcontroller 674 determines when the data acquisition system 638 acquires signals, stores the signals in the memory 622, or transmits data to the external device 108.

The switch 640 includes a plurality of switches for connecting the desired electrodes 200, 216-236 and input terminals 600-616 to the appropriate I/O circuits. The switch 640 closes and opens switches to provide electrically conductive paths between the circuitry of the IMD 102 and the input terminals 600-616 in response to a control signal 646. The impedance measuring circuit 620 may be electrically coupled to the switch 640 so that an impedance vector between any desired pairs of electrodes 200, 216-236 may be obtained. An atrial sensing circuit 648 and a ventricular sensing circuit 650 may be selectively coupled to the leads 204-208 (shown in FIG. 2) of the IMD 102 through the switch 640 for detecting the presence of cardiac activity in the chambers of the heart 106 (shown in FIG. 1). Control signals 652, 654 from the microcontroller 674 direct output of the atrial and ventricular sensing circuits 648, 650 that are connected to the microcontroller 674.

The memory 622 may be embodied in a computer-readable storage medium such as a ROM, RAM, flash memory, or other type of memory. The microcontroller 674 is coupled to the memory 622 by a suitable data/address bus 656. The memory 622 may store programmable operating parameters and thresholds used by the microcontroller 674, as required, in order to customize the operation of IMD 102 to suit the needs of a particular patient. The memory 622 may store data indicative of at least one of the cardiogenic impedance parameters and the electrophysiologic response parameters that may later be obtained to identify the potential cause of edema, as described above.

The operating parameters of the IMD 102 may be non-invasively programmed into the memory 622 through a telemetry circuit 658 in communication with the external device 108, such as a trans-telephonic transceiver or a diagnostic system analyzer. The telemetry circuit 658 is activated by the microcontroller 674 by a control signal 660. The telemetry circuit 658 allows intra-cardiac electrograms, cardiogenic impedance parameters, electrophysiologic response parameters, and status information relating to the operation of IMD 102 (as contained in the microcontroller 674 or memory 622), to be sent to the external device 108 through an established communication link 662. The IMD 102 additionally includes a battery 664 that provides operating power to the circuits shown within the housing 200, including the microcontroller 674. The IMD 102 also includes a physiologic sensor 666 that may be used to adjust pacing stimulation rate according to the exercise state of the patient.

In the case where IMD 102 is intended to operate as an ICD device, the IMD 102 detects the occurrence of a shift in one or more waveforms in detected cardiac signals that indicates an arrhythmia, and automatically applies an appropriate electrical shock therapy to the heart aimed at terminating the detected arrhythmia. To this end, the microcontroller 674 further controls a shocking circuit 668 by way of a control signal 670. The shocking circuit 668 generates shocking pulses of low (up to 0.5 joules), moderate (0.5-10 joules) or high energy (11 to 40 joules). Such shocking pulses are applied to the heart 106 (shown in FIG. 1) of the patient through at least two shocking electrodes, and as shown in this embodiment, selected from the housing 200, the left atrial coil electrode 224 (shown in FIG. 2), the RV coil electrode 234 (shown in FIG. 2), and/or the SVC coil electrode 236 (shown in FIG. 2).

Figure 8:
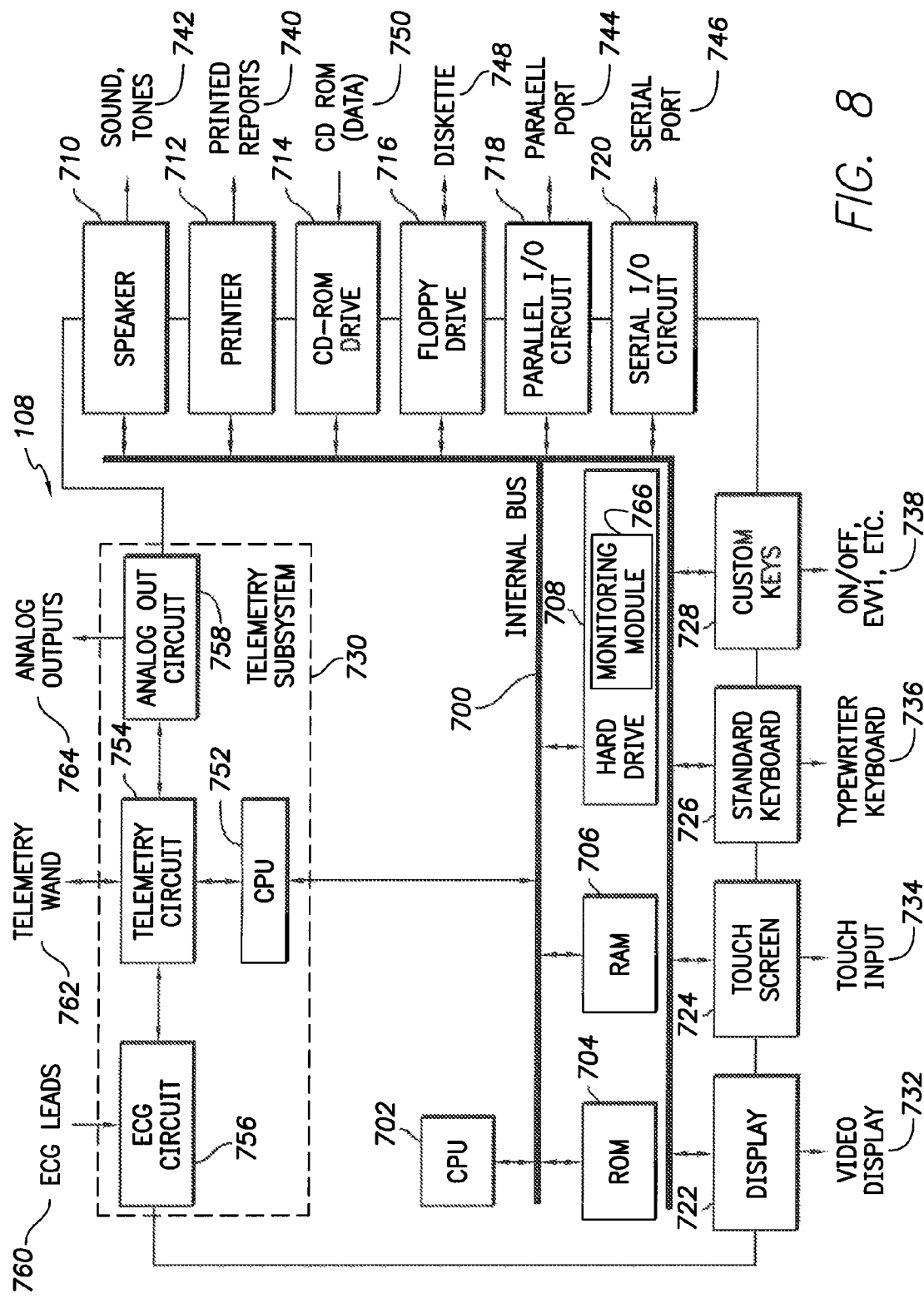
FIG. 8 illustrates a functional block diagram of the external device shown in FIG. 1 that is implemented in accordance with one example embodiment.

FIG. 8 illustrates a functional block diagram of the external device 108, such as a programmer, that is operated to interface with IMD 102. As described above, the external device 108 may be used by a physician or operator of the IMD 102 to monitor cardiogenic impedance parameters and electrophysiologic response parameters to identify a potential cause of pulmonary edema. The external device 108 includes an internal bus 700 that connects/interfaces with a Central Processing Unit (CPU) 702, ROM 704, RAM 706, a hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus 700 is an address/data bus that transfers information between the various components described herein. The hard drive 708 may store operational programs as well as data, such as cardiogenic impedance parameters and the electrophysiologic response parameters. The hard drive 708 includes a monitoring module 766 that monitors the cardiogenic impedance parameters and the electrophysiologic response parameters in order to identify a potential cause of pulmonary edema.

The CPU 702 typically includes a microprocessor, a microcontroller, or equivalent control circuitry, designed specifically to control interfacing with the external device 108 and with the IMD 102. The CPU 702 may include RAM or ROM memory 704, logic and timing circuitry, state machine circuitry, and I/O circuitry to interface with the IMD 102. The display 722 (e.g., may be connected to the video display 732) and the touch screen 724 display graphic information relating to the IMD 102. The touch screen 724 accepts a user's touch input 734 when selections are made. The keyboard 726 (e.g., a typewriter keyboard 736) allows the user to enter data to the displayed fields, as well as interface with the telemetry subsystem 730. Furthermore, custom keys 728 turn on/off 738 (e.g., EVVI) the external device 108. The printer 712 prints copies of reports 740 for a physician to review or to be placed in a patient file, and speaker 710 provides an audible warning (e.g., sounds and tones 742) to the user. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750.

The telemetry subsystem 730 includes a central processing unit (CPU) 752 in electrical communication with a telemetry circuit 754, which communicates with both an ECG circuit 756 and an analog out circuit 758. The ECG circuit 756 is connected to ECG leads 760. The telemetry circuit 754 is connected to a telemetry wand 762. The analog out circuit 758 includes communication circuits to communicate with analog outputs 764. The external device 108 may wirelessly communicate with the IMD 102 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 108 to the IMD 102.

Figure 9:
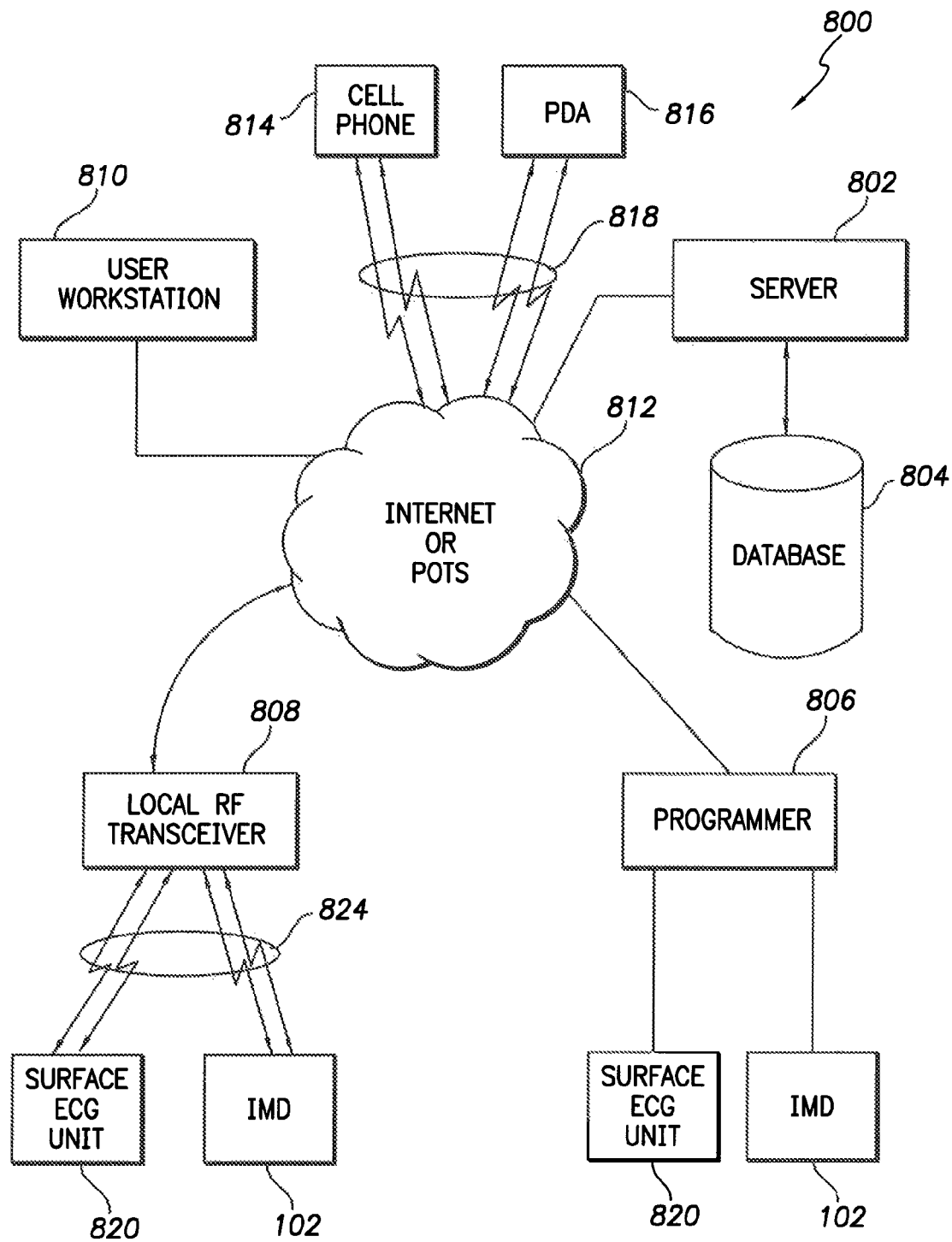
FIG. 9 illustrates a distributed processing system in accordance with one embodiment.

FIG. 9 illustrates a distributed processing system 800 in accordance with one embodiment. The distributed processing system 800 includes a server 802 connected to a database 804, a programmer 806 (e.g., similar to external device 108), a local RF transceiver 808 and a user workstation 810 electrically connected to a communication system 812. The communication system 812 may be the internet, a voice over IP (VoIP) gateway, a local plain old telephone service (POTS) such as a public switched telephone network (PSTN), a cellular phone based network, and the like. Alternatively, the communication system 812 may be a local area network (LAN), a campus area network (CAN), a metropolitan area network (MAN), or a wide area network (WAM). The communication system 812 serves to provide a network that facilitates the transfer/receipt of information such as cardiogenic impedance parameters and electrophysiologic response parameters.

The server 802 is a computer system that provides services to other computing systems over a computer network. The server 802 controls the communication of information such as cardiogenic impedance parameters and electrophysiologic response parameters. The server 802 interfaces with the communication system 812 to transfer information between the programmer 806, the local RF transceiver 808, the user workstation 810 as well as a cell phone 814, and a personal data assistant (PDA) 816 to the database 804 for storage/retrieval of records of information. On the other hand, the server 802 may upload raw cardiac signals from a surface ECG unit 820 or the IMD 102 via the local RF transceiver 808 or the programmer 806.

The database 804 stores information such as the measurements for the cardiogenic impedance parameters, the electrophysiologic response parameters, and the like, for a single or multiple patients. The information is downloaded into the database 804 via the server 802 or, alternatively, the information is uploaded to the server from the database 804. The programmer 806 is similar to the external device 108 and may reside in a patient's home, a hospital, or a physician's office. Programmer 806 interfaces with the surface ECG unit 820 and the IMD 102. The programmer 806 may wirelessly communicate with the IMD 102 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 806 to the IMD 102. The programmer 806 is able to acquire cardiac signals from the surface of a person (e.g., ECGs), intra-cardiac electrogram (e.g., IEGM) signals from the IMD 102, and/or values of cardiogenic impedance parameters and electrophysiologic response parameters from the IMD 102. The programmer 806 interfaces with the communication system 812, either via the internet or via POTS, to upload the information acquired from the surface ECG unit 820 or the IMD 102 to the server 802.

The local RF transceiver 808 interfaces with the communication system 812, via a communication link 824, to upload values of physiologic indices acquired from the surface ECG unit 820 and/or cardiogenic impedance parameters and electrophysiologic response parameters acquired from the IMD 102 to the server 802. In one embodiment, the surface ECG unit 820 and the IMD 102 have a bidirectional connection with the local RF transceiver via a wireless connection. The local RF transceiver 808 is able to acquire cardiac signals from the surface of a person, intra-cardiac electrogram signals from the IMD 102, and/or the values of cardiogenic impedance parameters and electrophysiologic response parameters from the IMD 102. On the other hand, the local RF transceiver 808 may download stored cardiogenic impedance parameters, electrophysiologic response parameters, cardiac data, and the like, from the database 804 to the surface ECG unit 820 or the IMD 102.

The user workstation 810 may interface with the communication system 812 via the internet or POTS to download values of the cardiogenic impedance parameters and electrophysiologic response parameters via the server 802 from the database 804. Alternatively, the user workstation 810 may download raw data from the surface ECG unit 820 or IMD 102 via either the programmer 806 or the local RF transceiver 808. Once the user workstation 810 has downloaded the cardiogenic impedance parameters and electrophysiologic response parameters, the user workstation 810 may process the information in accordance with one or more of the operations described above in connection with the process 400 (shown in FIG. 5). The user workstation 810 may download the information and notifications to the cell phone 816, the PDA 818, the local RF transceiver 808, the programmer 806, or to the server 802 to be stored on the database 804. For example, the user workstation 810 may communicate an identified potential cause of pulmonary edema to the cell phone 816 of a patient or physician.

Figure 10:
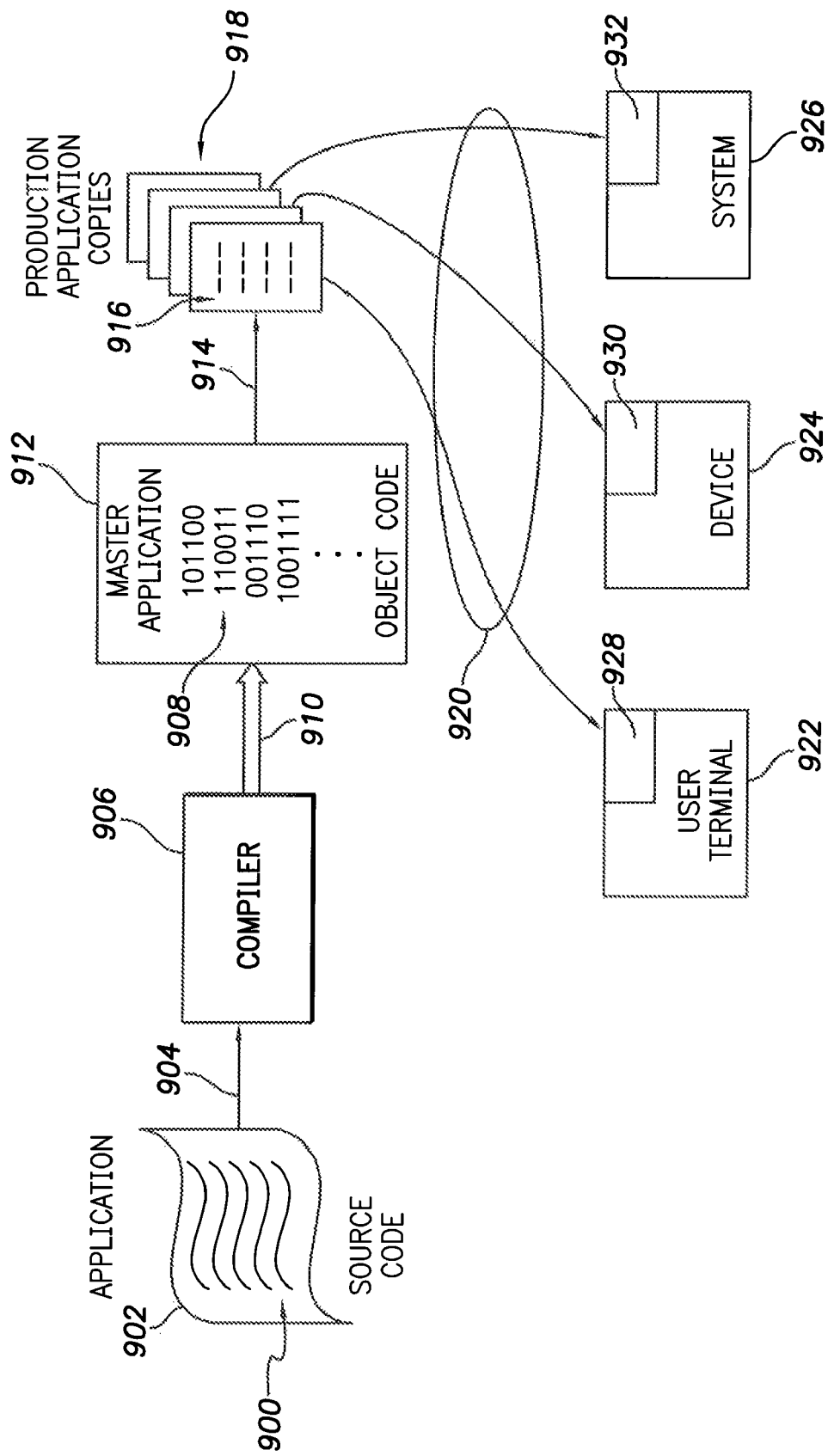
FIG. 10 illustrates a block diagram of example manners in which embodiments of the present invention may be stored, distributed, and installed on a computer-readable medium.

FIG. 10 illustrates a block diagram of exemplary manners in which embodiments of the present invention may be stored, distributed, and installed on a computer-readable medium. In FIG. 10, the "application" represents one or more of the methods and process operations discussed above. The application is initially generated and stored as source code 900 on a source computer-readable medium 902. The source code 900 is then conveyed over path 904 and processed by a compiler 906 to produce object code 908. The object code 908 is conveyed over path 910 and saved as one or more application masters on a master computer-readable medium 912. The object code 908 is then copied numerous times, as denoted by path 914, to produce production application copies 916 that are saved on separate production computer-readable medium 918. The production computer-readable medium 918 is then conveyed, as denoted by path 920, to various systems, devices, terminals and the like. A user terminal 922, a device 924 and a system 926 are shown as examples of hardware components, on which the production computer-readable medium 918 are installed as applications (as denoted by 928 through 932). For example, the production computer-readable medium 918 may be installed on the IMD 102 (shown in FIG. 1) and/or the microcontroller 674 (shown in FIG. 7). Examples of the source, master, and production computer-readable medium 902, 912, and 918 include, but are not limited to, CDROM, RAM, ROM, Flash memory, RAID drives, memory on a computer system, and the like. Examples of the paths 904, 910, 914, and 920 include, but are not limited to, network paths, the internet, Bluetooth, GSM, infrared wireless LANs, HIPERLAN, 3G, satellite, and the like. The paths 904, 910, 914, and 920 may also represent public or private carrier services that transport one or more physical copies of the source, master, or production computer-readable medium 902, 912 or 918 between two geographic locations. The paths 904, 910, 914 and 920 may represent threads carried out by one or more processors in parallel. For example, one computer may hold the source code 900, compiler 906 and object code 908. Multiple computers may operate in parallel to produce the production application copies 916. The paths 904, 910, 914, and 920 may be intra-state, inter-state, intra-country, inter-country, intra-continental, inter-continental, and the like.

The operations noted in FIG. 10 may be performed in a widely distributed manner world-wide with only a portion thereof being performed in the United States. For example, the application source code 900 may be written in the United States and saved on a source computer-readable medium 902 in the United States, but transported to another country (corresponding to path 904) before compiling, copying and installation. Alternatively, the application source code 900 may be written in or outside of the United States, compiled at a compiler 906 located in the United States and saved on a master computer-readable medium 912 in the United States, but the object code 908 transported to another country (corresponding to path 914) before copying and installation. Alternatively, the application source code 900 and object code 908 may be produced in or outside of the United States, but production application copies 916 produced in or conveyed to the United States (for example, as part of a staging operation) before the production application copies 916 are installed on user terminals 922, devices 924, and/or systems 926 located in or outside the United States as applications 928 through 932.

As used throughout the specification and claims, the phrases "computer-readable medium" and "instructions configured to" shall refer to any one or all of (i) the source computer-readable medium 902 and source code 900, (ii) the master computer-readable medium and object code 908, (iii) the production computer-readable medium 918 and production application copies 916 and/or (iv) the applications 928 through 932 saved in memory in the terminal 922, device 924, and system 926.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of identifying a potential cause of pulmonary edema comprising:
    obtaining one or more impedance vectors between predetermined combinations of electrodes positioned proximate a heart, at least one of the impedance vectors representative of a thoracic fluid level;
    applying a stimulation pulse to the heart;
    sensing cardiac signals of the heart that are representative of an electrophysiological response to the stimulation pulse; and
    monitoring the cardiac signals and at least one of the impedance vectors to determine whether a cardiac-related condition is the potential cause of pulmonary edema.

2. The method of claim 1, wherein the monitoring operation monitors one or more of a peak-to-peak parameter, a paced depolarization integral, and a slope of cardiac signal waveforms representative of the cardiac signals.

3. The method of claim 1, wherein the sensing operation senses the cardiac signals in connection with the stimulation pulse and by using the electrodes positioned proximate the heart.

4. The method of claim 1, wherein the obtaining operation comprises measuring a first impedance vector traversing at least a portion of a lung and a second impedance vector primarily traversing the heart.

5. The method of claim 4, wherein the first impedance vector is representative of a fluid level in the lung.

6. The method of claim 4, wherein the second impedance vector is representative of a fluid level in one or more chambers of the heart.

7. The method of claim 1, wherein the monitoring operation comprises determining if at least one of the cardiac signals and the impedance vectors follows a predetermined pattern with respect to time.

8. The method of claim 7, wherein the predetermined pattern is indicative of a decreasing trend in values of one or more of the cardiac signals and the impedance vectors respect to time.

9. The method of claim 1, wherein the monitoring operation identifies the potential cause of pulmonary edema as a cardiac-related condition when the cardiac signals and at least one of the impedance vectors follow one or more predetermined decreasing patterns with respect to time over a preset window.

10. The method of claim 1, wherein the monitoring operation identifies the potential cause of pulmonary edema as a cardiac-related condition when one or more of the cardiac signals and the impedance vectors indicate that a fluid level in one or more chambers of the heart is increasing with respect to time.

11. The method of claim 1, wherein the cardiac signals are representative of myocardial mass proximate one or more chambers of the heart.

12. The method of claim 1, further comprising initiating a responsive therapy in response to the potential cause of pulmonary edema identified by the monitoring operation.

13. An implantable medical device comprising:
    an excitation source configured to deliver stimulation pulses to a heart;
    electrodes configured to be positioned proximate the heart, the electrodes being capable of sensing cardiac signals of the heart that are representative of an electrophysiological response to at least one of the stimulation pulses;
    an impedance measuring module to obtain one or more impedance vectors between predetermined combinations of the electrodes positioned proximate the heart, at least one of the impedance vectors representative of a thoracic fluid level; and
    a monitoring module to monitor one or more parameters of the cardiac signals and at least one of the impedance vectors to determine whether a cardiac-related condition is a potential cause of pulmonary edema.

14. The device of claim 13, wherein the impedance measuring module obtains a first impedance vector traversing at least a portion of a lung and a second impedance vector primarily traversing the heart.

15. The device of claim 13, wherein the monitoring module determines if at least one of the cardiac signals and the impedance vectors follows a predetermined pattern with respect to time.

16. The device of claim 15, wherein the predetermined pattern is indicative of a decreasing trend in values of one or more of the cardiac signals and the impedance vectors with respect to time.

17. The device of claim 13, wherein the monitoring module identifies the potential cause of pulmonary edema as a cardiac-related condition when the cardiac signals and at least one of the impedance vectors follow one or more predetermined decreasing patterns with respect to time over a preset window.

18. The device of claim 13, wherein the monitoring module identifies the potential cause of pulmonary edema as a cardiac-related condition when one or more of the cardiac signals and the impedance vectors indicate that a fluid level in one or more chambers of the heart is increasing with respect to time.

19. The device of claim 13, wherein the cardiac signals are representative of myocardial mass proximate one or more chambers of the heart.

* * * * *